United States Patent [19]
Stevens et al.

[11] Patent Number: 5,776,767
[45] Date of Patent: Jul. 7, 1998

[54] VIRTUAL DNA SEQUENCER

[75] Inventors: John K. Stevens, Toronto; James M. Dunn, Scarborough; Gregory Dee, Toronto; James W. Cassidy, Waterloo, all of Canada

[73] Assignee: Visible Genetics Inc., Ontario, Canada

[21] Appl. No.: 570,994

[22] Filed: Dec. 12, 1995

[51] Int. Cl.$^6$ ................................................ C12M 3/00
[52] U.S. Cl. .................. 435/287.2; 204/608; 204/616; 356/344; 935/77; 935/87; 422/82.08; 422/129; 702/20
[58] Field of Search ................ 436/94; 435/287.2; 364/413.01; 382/129, 304; 935/77, 87; 204/608, 616; 356/344; 422/82.08, 119, 129

[56] References Cited

U.S. PATENT DOCUMENTS

| 4,811,218 | 3/1989 | Hunkapiller et al. | 364/413.01 |
| 5,502,773 | 3/1996 | Tibbets et al. | 382/129 |

FOREIGN PATENT DOCUMENTS

| 0294524 | 8/1988 | European Pat. Off. | G01N 27/26 |
| 0330897 | 2/1989 | European Pat. Off. | C12Q 1/68 |

OTHER PUBLICATIONS

Control and Instrumentation, vol. 26, No. 3, Mar. 1994, pp. 23-24, 26, "Data Acquisition".
Acquisition de Données, Comment Optimiser L'Échange des Données, Mar. 1994 No. 663, pp. 38+40+42.

*Primary Examiner*—David A. Redding
*Attorney, Agent, or Firm*—Oppedahl & Larson

[57] ABSTRACT

A virtual DNA sequencer combines a plurality of individual DNA sequencers. Samples of DNA or other nucleic acid from subjects are prepared and allocated in real time to particular lanes or sets of lanes in electrophoresis plates of the individual sequencers, with records kept of the allocations. The data resulting from the electrophoresis runs is collected and collated according to the identities of the subjects. The individual sequencers are networked, and each individual sequencer is preferably equipped with a data buffer large enough to accommodate all or substantially all of a data run, thus protecting the virtual sequencer from loss of valuable data in the event that the network is disrupted for some portion of the time of the data run. In this way, a plurality of sequencers is virtually the same as a single sequencer with a very large number of tracks each of which can run for a much longer sequencing run than an individual sequencer.

18 Claims, 8 Drawing Sheets

VIRTUAL DNA SEQUENCER

SPECIFICATION

The invention relates generally to DNA sequencers, and relates particularly to a novel approach for uniting a multitude of DNA sequencers into a large virtual DNA sequencer.

BACKGROUND

As more and more diseases are linked to genetic abnormalities, the possibility of diagnosis or of predictive screening for such diseases by sequencing an individual's nucleic acids takes on increasing significance. The first analytical methods for sequencing nucleic acids were slow and expensive. It is thus unsurprising that an extraordinary amount of effort has been directed in recent years to the task of sequencing nucleic acid sequences. The general approach is by now well known even to the general public: a sample of nucleic acid (typically DNA) is replicated (typically by PCR), decomposed into fragments, and passed through an electrophoresis gel. The fragments are tagged and detection of the tags permits determining the nucleotides making up the sequence. In a typical sequencer the tags are fluorescent tags, laser light is used to stimulate the tags, and photomultiplier tubes are used to detect the light that is given off by the fluorescent tags. Each sequencer contains a plate which is divided into a plurality of lanes, each one of which carries a sample being sequenced.

One of the steps in nucleotide sequence determination of a subject nucleic acid polymer is interpretation of the pattern of oligonucleotide fragments which results from electrophoretic separation of fragments of the subject nucleic acid polymer (the "fragment pattern"). The interpretation of the fragment pattern, colloquially known as "base-calling," results in determination of the order of four nucleotide bases, A (adenine), C (cytosine), G (guanine) and T (thymine) for DNA or U (uracil) for RNA in the subject nucleic acid polymer.

In the earliest method of base-calling, a method which is still commonly employed, the subject nucleic acid polymer is labeled with a radioactive isotope and either Maxam and Gilbert chemical sequencing (Proc. Natl. Acad. Sci. USA, 74: 560–564 (1977)) or Sanger et al. chain termination sequencing (Proc. Nat-l. Acad. Sci. USA 74: 5463–5467 (1977)) is performed. The resulting four samples of nucleic acid fragments (terminating in A, C, G, or T(U) respectively in the Sanger et al. method) are loaded into separate loading sites at the top end of an electrophoresis gel. An electric field is applied across the gel, and the fragments migrate through the gel. During this electrophoresis, the gel acts as a separation matrix. The fragments, which in each sample are of an extended series of discrete sizes, separate into bands of discrete species in a channel along the length of the gel. Shorter fragments generally move more quickly than larger fragments. After a suitable separation period, the electrophoresis is stopped. The gel may now be exposed to radiation sensitive film for the generation of an autoradiograph. The pattern of radiation detected on the autoradiograph is a fixed representation of the fragment pattern. A researcher then manually base-calls the order of fragments from the fragment pattern by identifying the step-wise sequence of the order of bands across the four channels.

More recently, with the advent of the Human Genome Organization and its massive project to sequence the entire human genome, researchers have been turning to automated DNA sequencers to process vast amounts of DNA sequence information. Existing automated DNA sequencers are available from Applied Diosystems, Inc. (Foster City, Calif.), Pharmacia Biotech, Inc. (Piscataway, N.J.), Li-Cor, Inc. (Lincoln, Nebr.), Molecular Dynamics, Inc. (Sunnyvale, Calif.) and Visible Genetics Inc. (Toronto). Automated DNA sequencers are basically electrophoresis apparatuses with detection systems which detect the presence of a detectable molecule as it passes through a detection zone. Each of these apparatus, therefore, are capable of real time detection of migrating bands of oligonucleotide fragments; the fragment patterns consist of a time based record of fluorescence emissions or other detectable signals from each individual electrophoresis channel. They do not require the cumbersome autoradhography methods of the earliest technologies to generate a fragment pattern.

The prior art techniques for computer-assisted base-calling for use in automated DNA sequencers are exemplified by the method of the Pharmacia A.L.F.™ sequencer. Oligonucleotide fragments are labeled with a fluorescent molecule such as fluorescein prior to the sequencing reactions. Sanger et al. sequencing is performed and samples are loaded into the top end of an electro)phoresis gel. Under electrophoresis the bands of species separate, and a laser at the bottom end of the gel causes the fragments to fluoresce as they pass through a detection zone. The fragment patterns are a record of fluorescence emissions from each channel. In general, each fragment pattern includes a series of sharp peaks and low, flat plains; the peaks representing the passage of a band of oligonucleotide fragments; the plains representing the absence of such bands.

To perform computer-assisted base-calling, the A.L.F. system executes at least four discrete functions: 1) it smooths the raw data with a band-pass frequency filter; 2) it identifies successive maxima in each data stream; 3) it aligns the smoothed data from each of the four channels into an aligned data stream; and 4) it determines the order of the successive maxima with respect to the aligned data stream.

Despite years of effort, sequencers continue to be slower and more expensive than would be desired.

In the pure research setting it is perhaps acceptable if a sequencer is slow and expensive, and if it is awkward to manage the data yielded by the sequencer But when it is desired to use DNA sequencers in a clinical diagnostic setting, several further problems arise. A first problem is that each DNA sequencer is treated as an isolated individual system and data must be transferred via a floppy disk or over a network connection to a central computer.

The sheer size of the human genome makes it unrealistic to sequence the entirety of the DNA of a patient, so instead it is commonplace to sequence a number of exons, portions c.f genetic material that are thought to be of interest. This leads to a bookkeeping or paperwork task. In a clinical diagnostic setting, where several exons are to be sequenced for each of thousands of patients, a technician has to deep track of information regarding which exon was run in which lane of which gel plate. Analysis of the resulting data requires transferring files from one floppy disk to another so that an individual exon may be compared with another exon. This is shown schematically in FIG. 1, where the outputs of several sequencers 20a, 20b, etc. are received on floppy disks 21a, 21b, etc. The disks are distributed manually through what is colloquially termed a "sneaker net" or "Nike™ net" (named after the well-known brand of athletic shoes). A series of manual and error-prone steps can lead to data being stored according to particular patient folders 23a, 23b. Similarly if exons are to be compared, this too requires manual steps via the "sneaker net".

3

As suggested in prior art FIG. 2, some prior-art sequencer systems permit connection of sequencers to each other, and to one or more hosts, via a network 24. Or, more commonly, each sequencer 20a, 20b is connected by a dedicated serial link to a personal computer, and the personal computers are connected by a network. In any of these cases, some computer 27 eventually comes to hold files 25a, 25b etc. which represent data collected in the sequencing activities of the sequencers 20a, 20b etc. For exons to be compared, or for results relating to a particular patient task to be stored together, time-consuming and error-prone manual manipulations 26 are required. The "sneaker network" of FIG. 1 is replaced in part by a network 4, but the time-consuming and error-prone manual manipulations remain.

A further difficulty in a clinical diagnostic setting is that it is awkward or impossible to assign separate tests to separate lanes for different patients. Capacity of the gels is compromised and as a result, often a gel is run with empty lanes.

Analyzing data from different exons from the same patient is very difficult, because in most cases the exons were run on different DNA sequencers on different days, and have been stored in many different disks. Comparing the same exon from many different patients is also difficult for the same reasons.

To be sure the PCR chemistry worked properly, it is often necessary to run the PCR products on a gel. In general such runs could be run on the same gels used for DNA sequencing. Because it is difficult to keep track of results, these are often run as separate batches on one DNA sequencer. This also can waste gel lane space.

SUMMARY OF THE INVENTION

In keeping with the invention, a virtual DNA sequencer combines a plurality of individual DNA sequencers. Samples of DNA or other nucleic acid from subjects are prepared and allocated in real time to particular lanes or sets of lanes in electrophoresis plates of the individual sequencers, with records kept of the allocations. The data resulting from the electrophoresis runs is collected and collated according to the identities of the subjects. The individual sequencers are networked, and each individual sequencer is preferably equipped with a data buffer large enough to accommodate all or substantially all of a data run, thus protecting the virtual sequencer from loss of valuable data in the event that the network is disrupted for some portion of the time of the data run. In this way, a plurality of sequencers is virtually the same as a single sequencer with a very large number of tracks each of which can run for a much longer sequencing run than an individual sequencer.

DESCRIPTION OF THE DRAWINGS

The drawing will be described in connection with a drawing in several figures, of which:

FIG. 5B shows a

Figure 6:
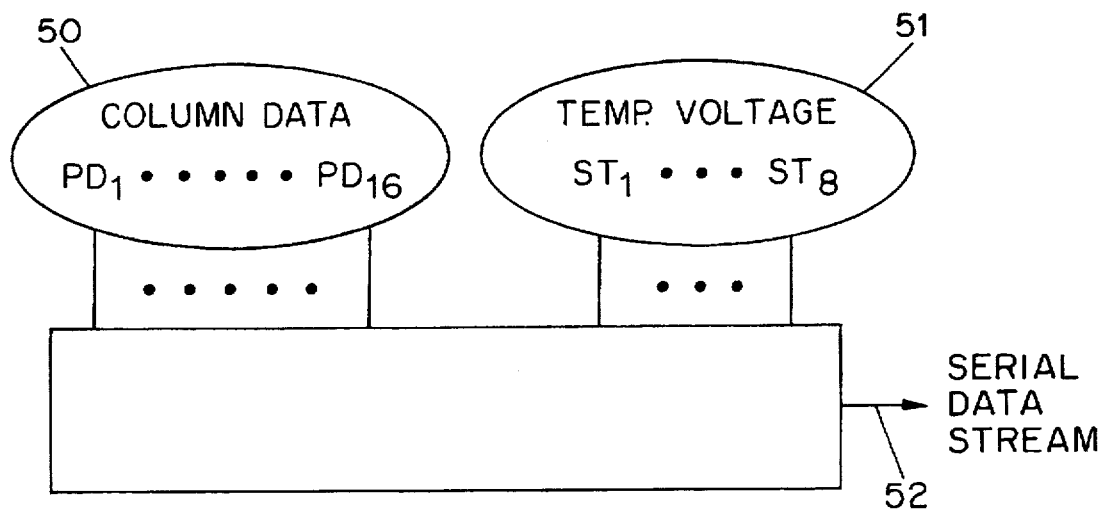
Figure 7:
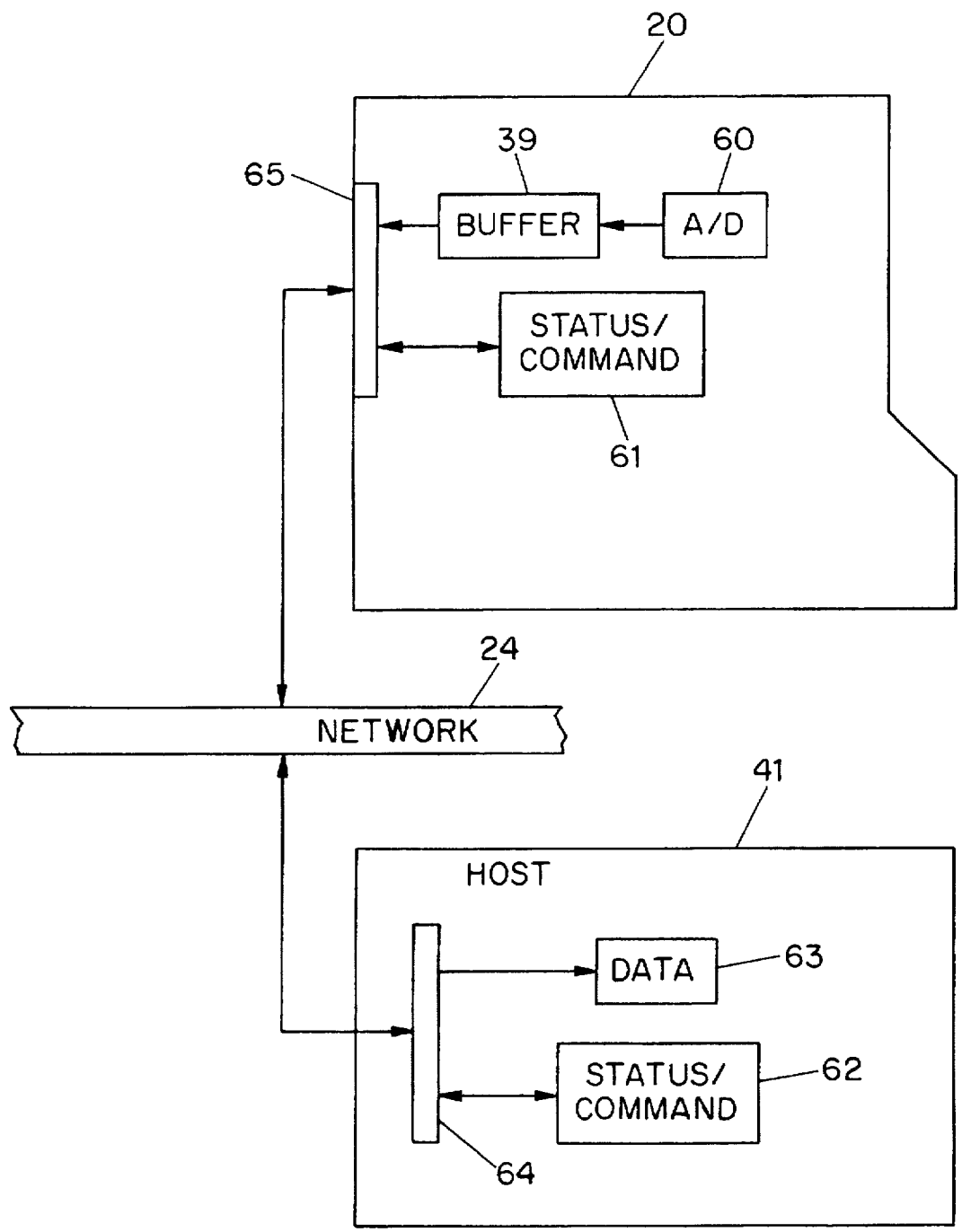
Figure 8:
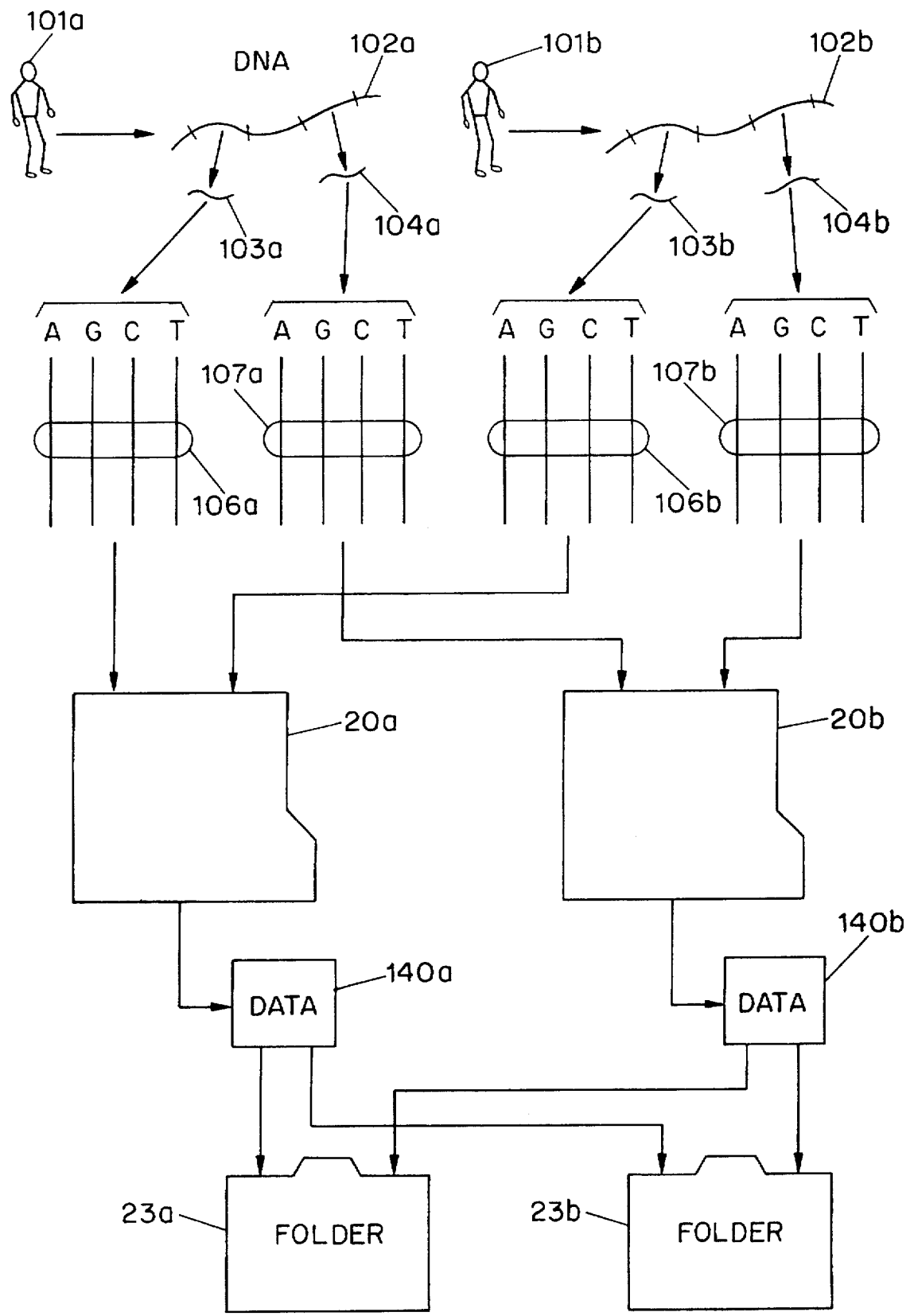
Figure 9:
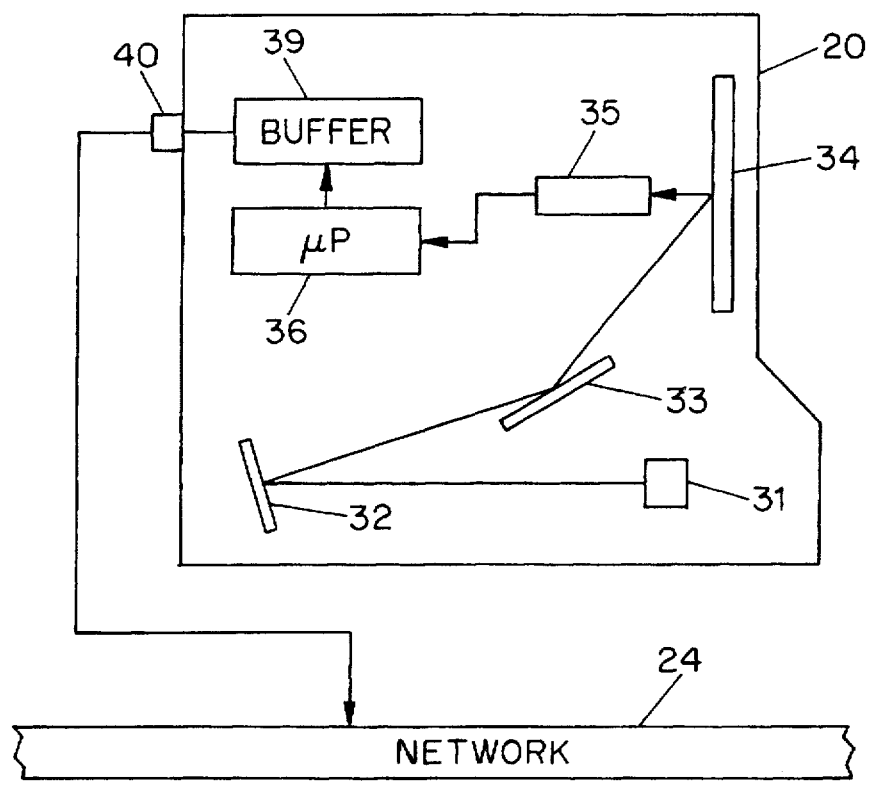
Figure 10:
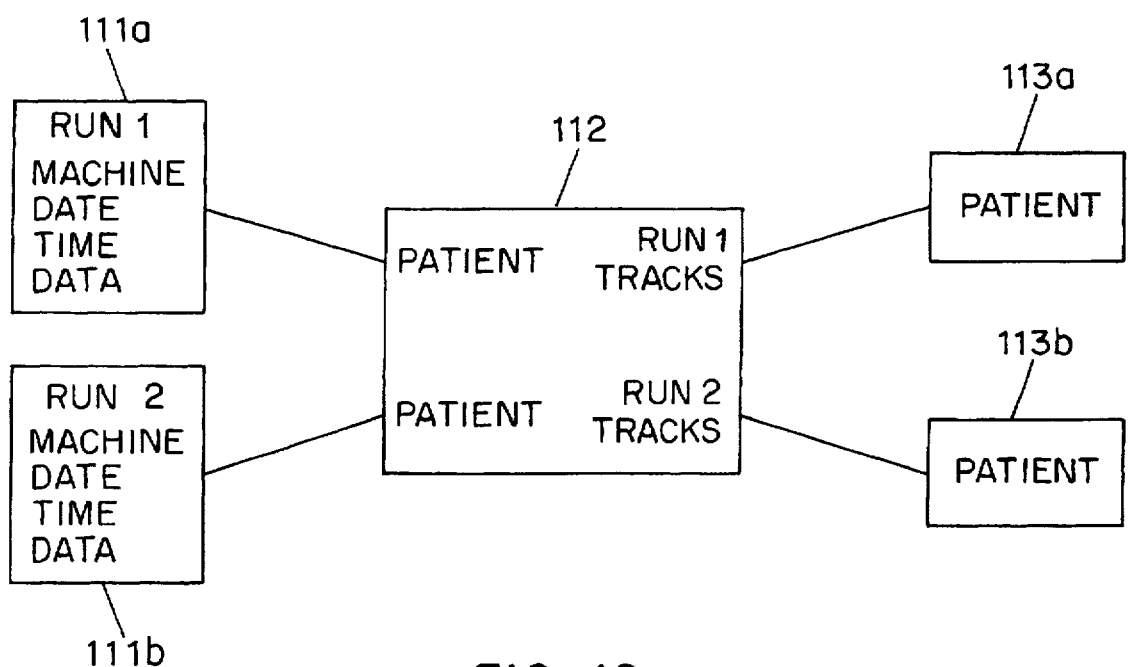

4 different protocol-level link between the sequencer and the host computer;

FIG. 6 shows inputs in a sequencer that are serialized into a serial data stream;

FIG. 7 shows a protocol-level link between a sequencer and a host computer, including two signaling channels;

FIG. 8 shows in dataflow form the data propagation relating to two subjects, their DNA, and the analysis and data storage for the subjects;

FIG. 9 shows in functional block diagram for an individual DNA sequencer forming part of a virtual sequencer including a data buffer; and FIG. 10 depicts data elements relating to the virtual sequencer of the invention and relations therebetween.

Where possible, like items have been shown with like reference numerals.

DETAILED DESCRIPTION

Figure 1:
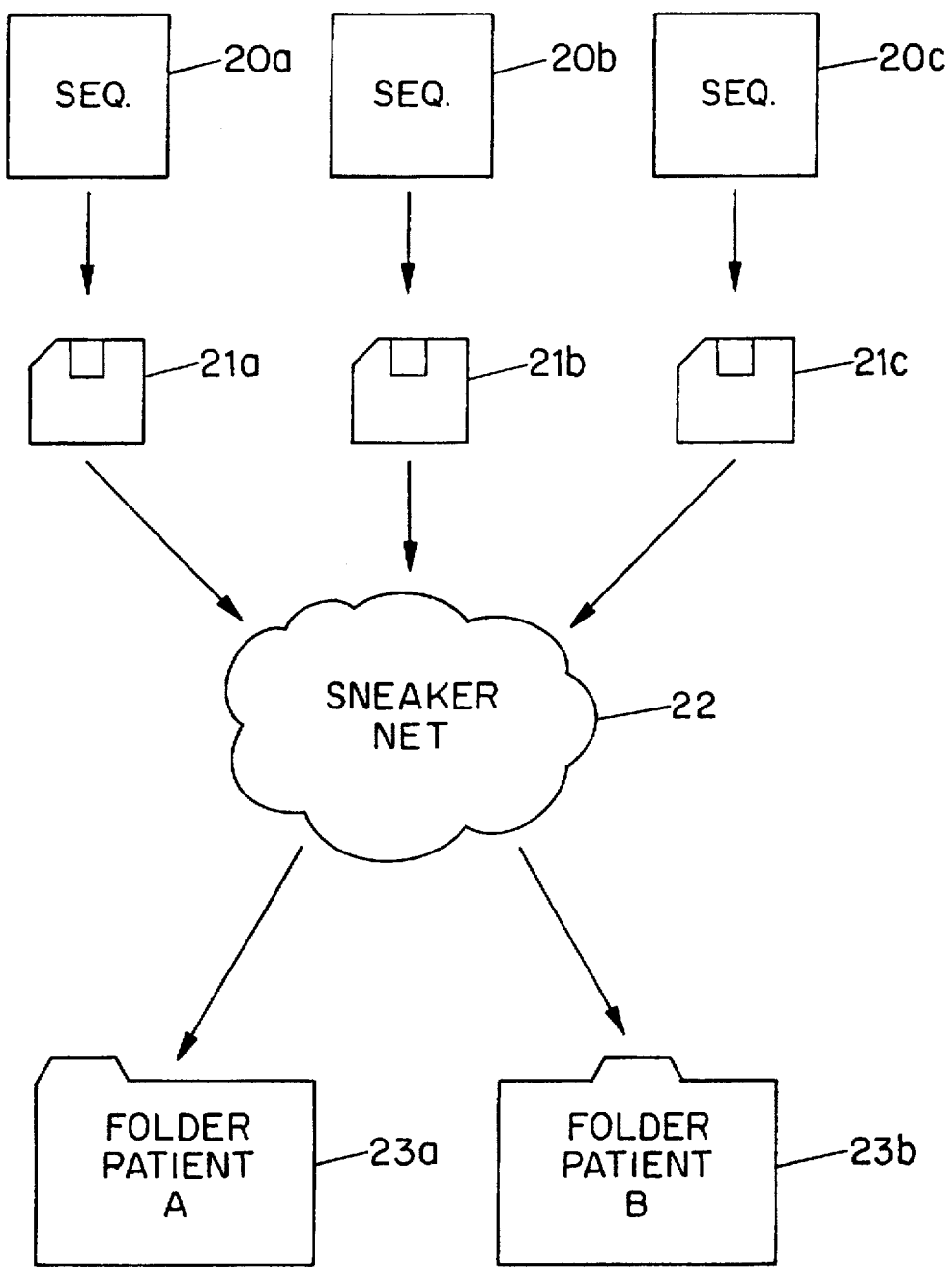
FIG. 1 is a prior art portrayal of a group of DNA sequencers.
Figure 2:
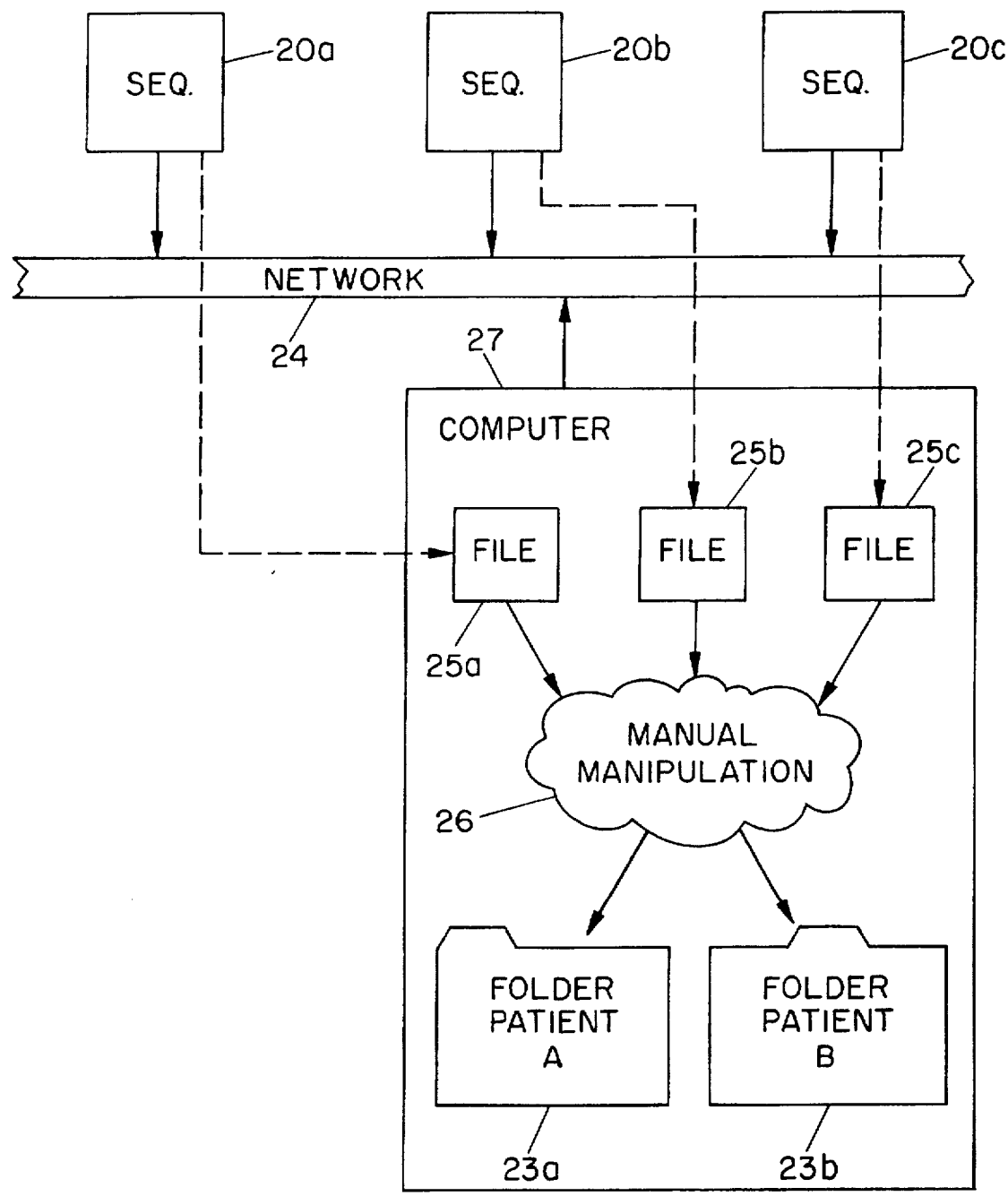
FIG. 2 is a prior art portrayal of a group of DNA sequencers tied together in a network.
Figure 3:
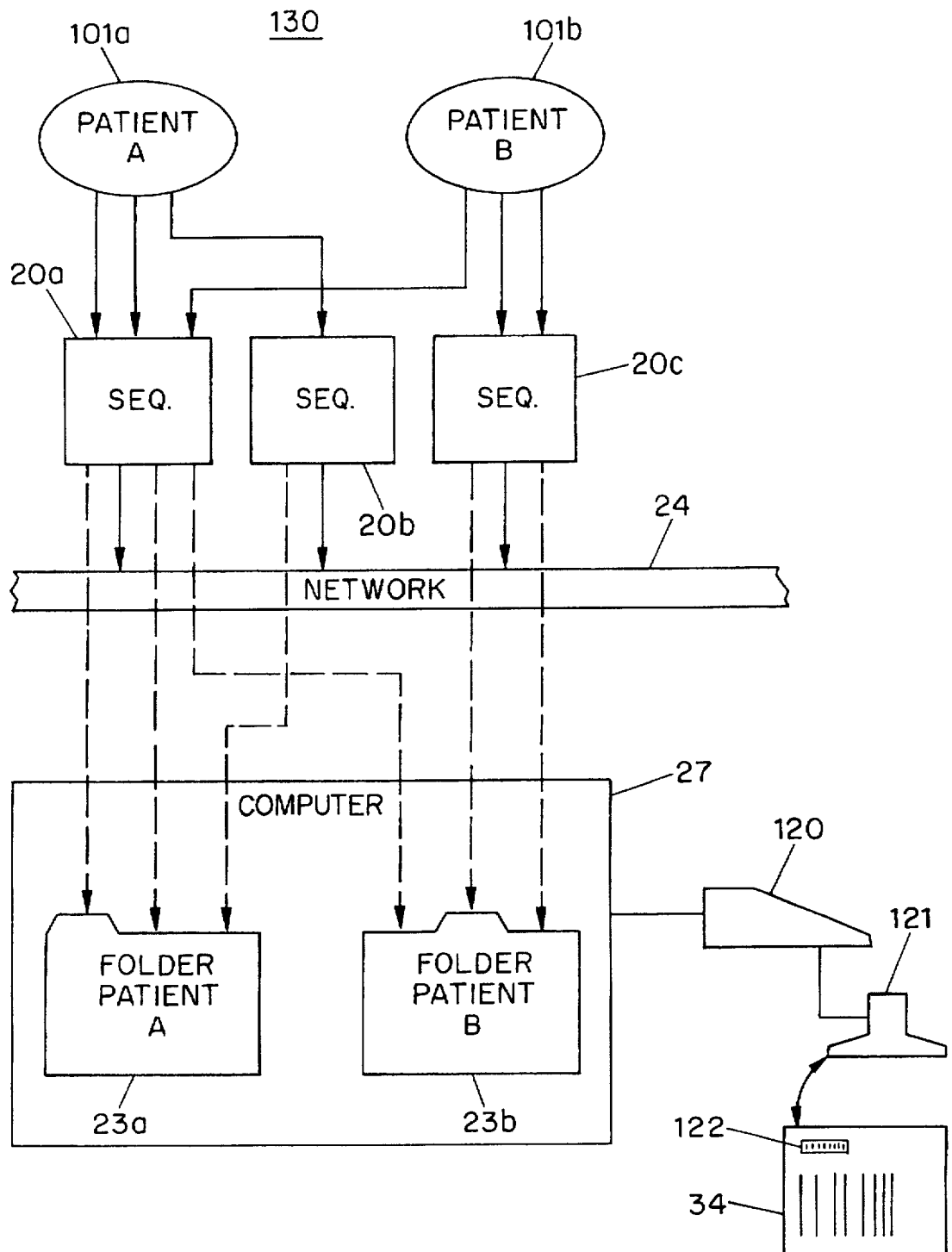
FIG. 3 is a portrayal of a group of DNA sequencers comprising a virtual DNA sequencer, according to the invention.

FIG. 3 shows in functional block diagram form an embodiment of the virtual sequencer 130 according to the invention. The virtual sequencer 130 may be thought of as an instrumentality that receives a sample or group of samples of nucleic acid material from a patient A 101a, and in a more or less automatic and reliable way the analytical result of the sequencing work appears in a folder 23a, as suggested by the solid and dotted arrows. It is almost as if there were a single sequencer with the capability of handling all of the sequencing needs for the task of patient 101a in a single data run. Similarly, and simultaneously, the instrumentality receives a sample or group of samples from patient 101b, and that, too, leads to a folder 23b. The virtual sequencer is or may be much bigger than that shown in FIG. 3, accommodating a large number of individual sequencers and patient sequencing tasks at a particular time. The manner in which this virtual sequencer accomplishes its goals is set forth in detail below.

Figure 4:
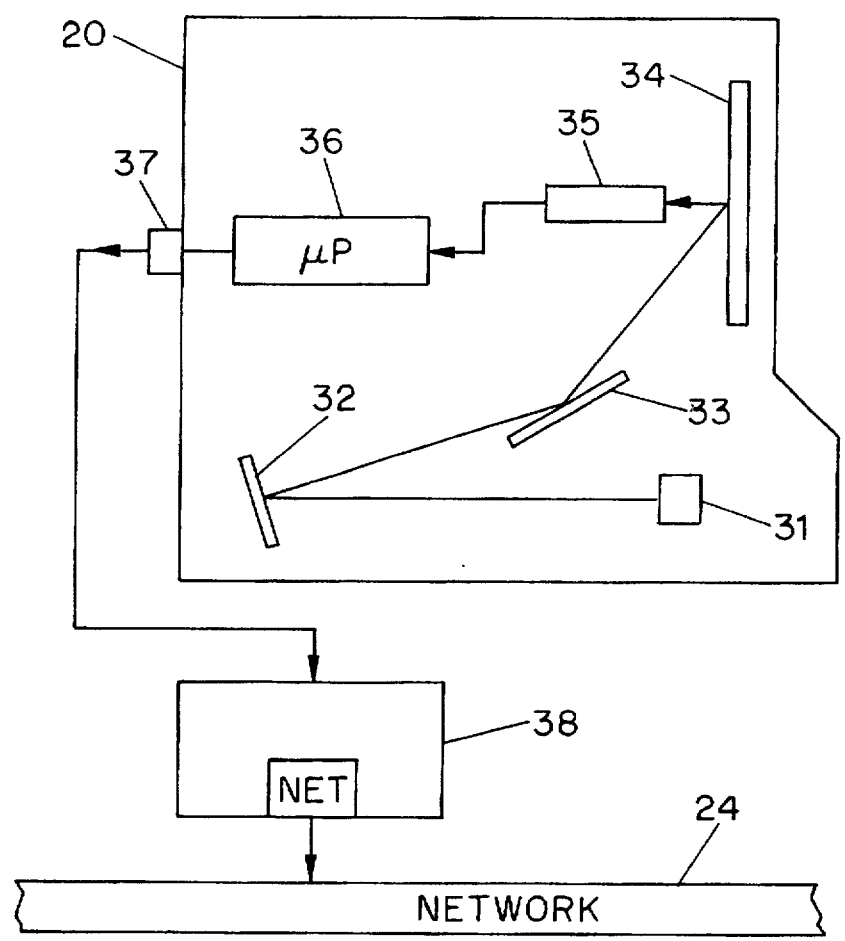
FIG. 4 is a functional block diagram of an individual DNA sequencer forming part of a virtual sequencer.

FIG. 4 shows a typical and preferred individual sequencer that makes up a portion of the virtual sequencer according to the invention. As set forth more fully in U.S. application Ser. No. 08/353,932 which is incorporated by reference and in application Ser. No. PCT/US95 15951 (attorney docket no. VGENP009WO, designating the United States and filed on even date herewith) which is incorporated by reference, the sequencer starts with a laser diode 31. The laser diode 31 emits a laser beam which reflects from mirror 32 and mirror 33 to form an illuminated region within electrophoresis plate 34. The plate 34 may preferably be that set forth in copending appliation Ser. No. 08/332,577 incorporated herein by reference.

From time to time, the nucleic acid fragments that propagate through the plate 34 present fluorescence in the detection area of the plate 34 as is well known to those skilled in the art of fluorescent-tagged nucleic acid electrophoresis. The emitted light is received in photodiode detectors 35. The signal from a detector 35 is converted to digital form in an A/D convertor, preferably in the manner set forth in copending application Ser. No. 08/497,202, incorporated herein by reference. The digital data stream is handled by a processor circuit board 36, and is passed through a conventional serial port 37. In the system according to the invention this serial data passes to a protocol convertor 38 which is connected to a network 24.

As described in pending U.S. application Ser. No. 08/452,719, which is incorporated herein by reference, the sequencer is made up of a plurality of detection areas, each of which receives radiation from an electromagnetic radiation emitter. The number of detection areas is preferably a multiple of 4, such as 16 or 40. Each detection area lies in a "track" running in the direction of the voltage gradient. The electromagnetic radiation generated in the detection area is detected by an electromagnetic radiation detector 35. The detector has an electrical output indicative of detected electromagnetic radiation.

Figure 5A:
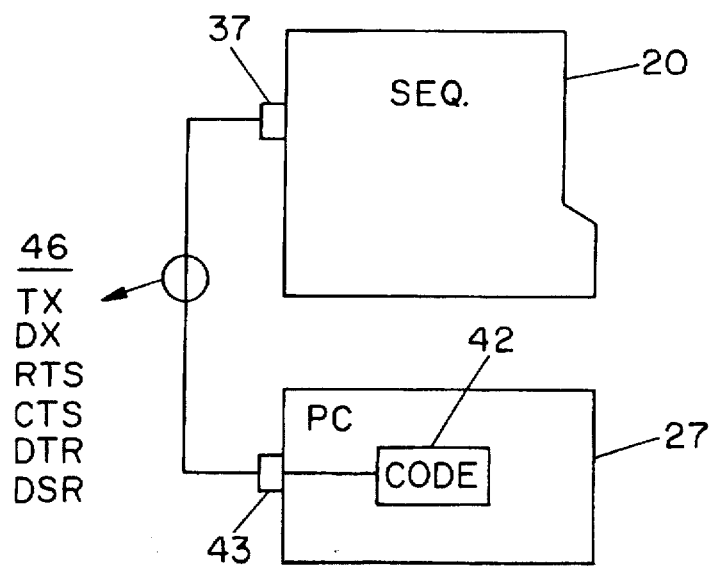
FIG. 5A shows the protocol-level link between a sequencer and a host computer.

Turning now to FIG. 5A there is shown a sequencer 20 of a type with a serial output port 37. The communications channel from port 37 is a serial data link 46 such as an RS-232 link, to a serial input port 43 of a host, typified by personal computer 27. Software 42 in the computer receives the data stream via the serial port 43. The typical handshake lines request-to-send, clear-to-send, data-terminal-ready and data-set-ready are employed along with a transmit data line and a receive data line.

Turning momentarily to FIG. 6 there is shown in input-output form a typical data flow in the sequencer. This sequencer has sixteen tracks and data channels 50 which provide a sixteen-bit word to be communicated externally from the sequencer. In addition, it is preferable to provide eight sixteen-bit words of status information 51 in the data stream, indicative of the electrophoresis voltage, plate temperature, and other important information. Thus, each packet of data contains twenty-four words or forty-eight bytes of data.

In one sequencer system it has been established to provide one packet per second. However, with advances in sequencing speed (as described in the above-referenced copending patent applications) there is the possibility that an event of interest would be missed if data were only collected once per second. Thus, it is considered preferable to provide such a packet every 250 msec, or four packets per second.

Figure 5B:
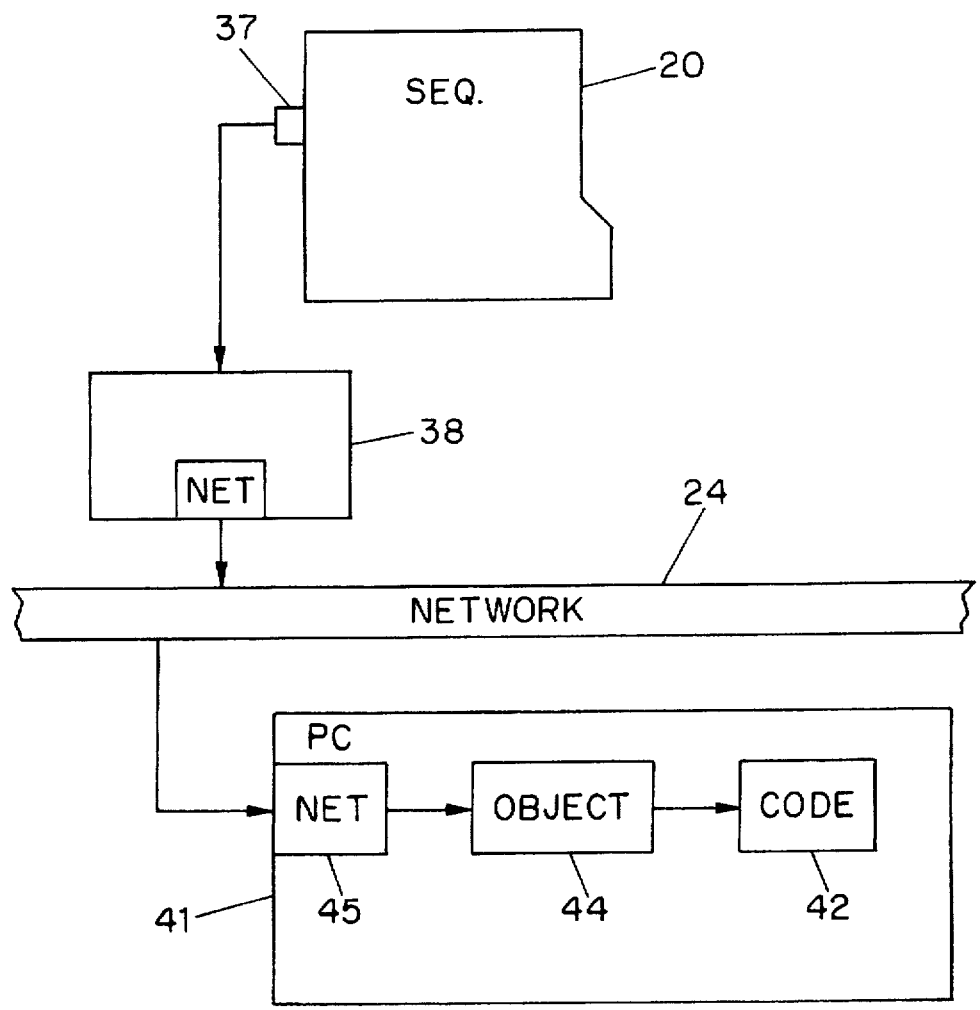

Returning now to FIG. 5B there is shown a system like that of FIG. 5A, except that a protocol conversion box 38 is connected between the serial port 37 and the network 24. The PC 41 has a network interface card 45. A software object 44 is interposed between the software 42 and the network interface card 45. The result of the software object 44 is that from the point of view of the software 42 the connection is identical to that of FIG. 5A; the software 42 need not be changed despite introduction of the protocol convertor 38.

Turning now to FIG. 7 there is shown a sequencer 20 and host computer 41 in more detail, in a preferred embodiment. The sensors provide analog signals to an A/D convertor 6C. The output of the A/D convertor 60 is buffered in a buffer 39. This buffer is selected to be a size comparable to the entire data output of the sequencing run of the sequencer 20. For example, in the case where a 48-byte packet is sent every 250 msec., then the data rate is about 192 bytes per second. If a buffer 39 of 1.2 MB (megabytes) is provided, then about 100 minutes of data may be stored. On the other hand, the buffer might be as little as 1 MB or as much as 2 MB.

Stated differently, there is simply a 1.2 MB data storage capacity in each machine. Under normal operation, the data from the sequencer feeds into this memory buffer 39. The data is periodically called for over the network 24 by computer workstations such as host 41, on the network 24. The crucial advantage for this is that if the network 24 fails, then the data is not lost. When the network 24 is reactivated, the workstation 41 samples the memory buffer 39 to recover any data not yet sent.

This may be compared, for example, with the sequencer of FIG. 5A, which has its own PC 27 attached directly to it. Such a sequencer has no substantial onboard memory devices. If the PC 27 crashes, then the data run from the individual sequencer 20, prior to PC reactivation, may be lost. Fortunately, PC's don't crash as often as networks, so problems are relatively.

FIG. 9 shows the sequencer of FIG. 7 in greater detail. With this arrangement, a fully buffered machine 20 can be networked to a much broader network 24, and it is not absolutely required that the network 24 be perfectly reliable. In contrast, many prior-art sequencers have no onboard memory 39. If the system fails to collect the sequencer data when it is ready, the sequencer data is lost. The result can be loss of an expensive data run.

The significance of the relationship between the sequencer 20 and the host personal computer 41 (FIG. 7) may be contrasted with that between a computer and, say, a laser printer, which is a sink for data rather than a source.

The extent of the benefit offered by the buffer 29 differs depending on the type of network 24 being used, for example 10Base2 (thin co-axial) and 10BaseT (twisted pair). 10BaseT is cheaper, more resilient, and has a spider topology with a concentrator; and the concentrator rarely goes down. Generally one worries more about a machine crash more than about a network crash. In contrast, where 10Base2 is used, the probability of net crashing is more common because each link must be contained.

Returning to FIG. 7, it was mentioned that the size of the buffer can be anywhere from 1 to 2 MB of data storage. The amount depends on the number of lanes and the sampling rate being used. As mentioned above, the number of lanes may be anywhere in the range of 16 to 40, while the sampling rate may be anywhere from 1 to 4 Hz.

FIG. 10 depicts pictorially some of the data types that may be used in the system according to the invention. Blocks 111a and 111b represent the raw data from the sequencing machine data runs. Blocks 113a and 113b represent data grouped according to the patient or analysis subject. Block 112 represents laboratory plan data indicating which tracks for a particular sequencer's run are associated with one task (e.g. a section of a patient's DNA) and which are associated with a different task.

It is noted that the data passed from the sequencers 20 to the system are "raw data" from the sensors 35 (FIG. 4) and are not nucleotide values. That is, the "base calling" process has not yet occurred at the time the sequencer passes its data to the system. Indeed, it is a preferable aspect of the invention that the raw data are passed in their entirety (or substantially unchanged) to the folders 23a, 23b as suggested in FIG. 8. In this way, even after the patient data have been collected together, it is possible to go back and do the "base calling" again and again in the event that some ambiguity presents itself. Similarly, if it is desired to collect and display several instances of a particular exon (from several different subjects, say) as part of a study or as part of an effort to resolve a base calling ambiguity, the raw data will have been retained permitting such study.

It will thus be appreciated that what has been provided is a virtual sequencer, a system composed of a plurality of individual sequencers. It seamlessly tracks the sub-tasks that make up a sequencing task, permitting the sub-tasks to be split up over several sequencers, and permitting the straightforward collation of the resulting sequence data for study by patient, by task, or by exon. It is as if one had a single sequencer with arbitrarily many electrophoresis tracks, to accommodate an arbitrarily large sequencing task. It is as if one had a sequencer that could sequence far more base pairs in a run than one sequencer can sequence, insofar as the data are seamlessly reassembled after a too-large task has been broken up according to the actual base-pair capacity of the sequencers.

It will thus be appreciated by those skilled in the art that the system set forth above may be accomplished by providing within the host computer first, second, and third means. A first means within the host responds to inputs at the terminal for storing, within the data store, first records associating the first subject with a first particular lane of the first individual sequencer and with a first particular lane of the second individual sequencer, and associating the second subject with a second particular lane of the first individual sequencer and with a second particular lane of the second individual sequencer. A second means within the host receives the outputs of the detector means of the first and second individual sequencers and stores, within the data store, second records representative of the outputs and indicative of the lanes of the individual sequencers providing the outputs. Finally, a third means within the host receives the first and second records, and in response thereto, stores third records, each of said third records comprising data from particular lanes corresponding to a particular one of the subjects.

Those skilled in the art will have no difficulty devising countless obvious variations of the invention without departing in any way from the invention, all of which are intended to be encompassed by the claims which follow.

We claim:

1. A virtual nucleic acid sequencer for use in sequencing respective samples of nucleic acids from first and second subjects, the virtual sequencer comprising:

at least first and second individual nucleic acid sequencers, each of said individual sequencers comprising at least two lanes, each of said lanes having a respective analysis region, each of said individual sequencers further comprising detector means optically coupled with said at least two lanes, said detector means having an output indicative of optical activity in its respective analysis regions, each of said individual sequencers further comprising buffer means associated with the respective detector means, said buffer sized to accommodate substantially all the output from the sequencing of the nucleic acid sample from one of the subjects;

a host;

an input terminal communicatively coupled with the host;

a data store communicatively coupled with the host;

a communications channel communicatively coupling the buffer means associated with the detector means of the first and second individual sequencers with the host;

first means within the host for responding to inputs at the terminal for storing, within the data store, first records associating the first subject with a first particular lane of the first individual sequencer and with a first particular lane of the second individual sequencer, and associating the second subject with a second particular lane of the first individual sequencer and with a second particular lane of the second individual sequencer; and second means within the host for receiving the outputs of the detector means of the first and second individual sequencers and storing, within the data store, second records representative of the outputs and indicative of the lanes of the individual sequencers providing the outputs;

third means within the host for receiving the first and second records, and in response thereto, for storing third records, each of said third records comprising data from particular lanes corresponding to a particular one of the subjects.

2. The virtual sequencer of claim 1 wherein each of the buffer means is at least one megabyte in size.

3. The virtual sequencer of claim 2 wherein each of the buffer means is at least two megabytes in size.

4. The virtual sequencer of claim 1 wherein each of the individual sequencers has at least sixteen lanes.

5. The virtual sequencer of claim 4 wherein each of the individual sequencers has at least twenty-four lanes.

6. The virtual sequencer of claim 1 wherein the detector means of each individual sequencer generates its output no less often than once per second.

7. The virtual sequencer of claim 6 wherein the detector means of each individual sequencer generates its output no less often than once per 250 milliseconds.

8. The virtual sequencer of claim 1 wherein the number of individual sequencers is no fewer than four.

9. The virtual sequencer of claim 1 wherein the communications channel comprises a network.

10. The virtual sequencer of claim 1 wherein the input terminal further comprises a bar-code reader and wherein the tracks are labeled with bar codes, the inputs at the input terminal comprising bar code data read by the bar code reader.

11. A virtual nucleic acid sequencer for use in sequencing nucleic acids from first and second subjects, the virtual sequencer comprising:

at least first and second individual nucleic acid sequencers, each of said individual sequencers comprising at least two lanes, each of said lanes having a respective analysis region, each of said individual sequencers further comprising detector means optically coupled with said at least two lanes, said detector means having an output indicative of optical activity in its respective analysis regions;

a host;

a terminal communicatively coupled with the host;

a data store communicatively coupled with the host;

a communications channel communicatively coupling the outputs of the detector means of the first and second individual sequencers with the host;

first means within the host for storing, within the data store, first records associating the first subject with a first particular lane of the first individual sequencer and with a first particular lane of the second individual sequencer, and associating the second subject with a second particular lane of the first individual sequencer and with a second particular lane of the second individual sequencer; and second means within the host for receiving the outputs of the detector means of the first and second individual sequencers and storing, within the data store, second records representative of the outputs and indicative of the lanes of the individual sequencers providing the outputs;

third means within the host for receiving the first and second records, and in response thereto, for storing third records, each of said third records comprising data from particular lanes corresponding to a particular one of the subjects.

12. The virtual sequencer of claim 11 wherein each of the individual sequencers has at least sixteen lanes.

13. The virtual sequencer of claim 12 wherein each of the individual sequencers has at least twenty-four lanes.

14. The virtual sequencer of claim 11 wherein the detector means of each individual sequencer generates its output no less often than once per second.

15. The virtual sequencer of claim 14 wherein the detector means of each individual sequencer generates its output no less often than once per 250 milliseconds.

16. The virtual sequencer of claim 11 wherein the number of individual sequencers is no fewer than four.

17. The virtual sequencer of claim 11 wherein the communications channel comprises a network.

18. The virtual sequencer of claim 11 wherein the input terminal further comprises a bar-code reader and wherein the tracks are labeled with bar codes, the inputs at the input terminal comprising bar code data read by the bar code reader.

* * * * *